US00PP30266P2

(12) United States Plant Patent
Hofmann

(10) Patent No.: US PP30,266 P2
(45) Date of Patent: Mar. 5, 2019

(54) ***MANDEVILLA* PLANT NAMED 'INMANPINLI'**

(50) Latin Name: *Mandevilla sanderi*
Varietal Denomination: Inmanpinli

(71) Applicant: Birgit Hofmann, Rudesheim am Rhein (DE)

(72) Inventor: Birgit Hofmann, Rudesheim am Rhein (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 0 days.

(21) Appl. No.: 15/732,270

(22) Filed: Oct. 17, 2017

(51) Int. Cl.
*A01H 5/02* (2018.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — C. A. Whealy

(57) ABSTRACT

A new and distinct cultivar of *Mandevilla* plant named 'Inmanpinli', characterized by its upright and vining plant habit; vigorous growth habit; freely branching habit; glossy medium green-colored leaves; freely flowering habit; and light red purple-colored flowers that resist fading.

2 Drawing Sheets

Botanical designation: *Mandevilla sanderi.*
Cultivar denomination: 'INMANPINLI'.

BACKGROUND OF THE INVENTION

The present invention relates to a new and distinct cultivar of *Mandevilla* plant, botanically known as *Mandevilla sanderi* and hereinafter referred to by the name 'Inmanpinli'.

The new *Mandevilla* plant is a product of a planned breeding program conducted by the Inventor in Gensingen, Germany and Johannesburg, South Africa. The objective of the breeding program is to create new freely branching *Mandevilla* plants that flower freely and have attractive flowers that resist fading and sun scald.

The new *Mandevilla* plant originated from a cross-pollination conducted by the Inventor in Gensingen, Germany in June, 2008 of *Mandevilla sanderi* 'Rio White', not patented, as the female, or seed parent with *Mandevilla sanderi* 'Rio Deep Red', not patented, as the male, or pollen, parent. The new *Mandevilla* plant was discovered and selected by the Inventor as a single flowering plant from within the progeny of the stated cross-pollination in a controlled greenhouse environment in Johannesburg, South Africa in December, 2009.

Asexual reproduction of the new *Mandevilla* plant by vegetative cuttings in a controlled greenhouse environment in Johannesburg, South Africa since March, 2010 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inmanpinli'. These characteristics in combination distinguish 'Inmanpinli' as a new and distinct *Mandevilla* plant:

1. Upright and vining plant habit.
2. Vigorous growth habit.
3. Freely branching habit.
4. Glossy medium green-colored leaves.
5. Freely flowering habit.
6. Light red purple-colored flowers that resist fading.

Plants of the new *Mandevilla* can be compared to plants of the female parent, 'Rio White'. Plants of the new *Mandevilla* differ primarily from plants of 'Rio White' in the following characteristics:

1. Plants of the new *Mandevilla* are more freely branching than plants of 'Rio White'.
2. Plants of the new *Mandevilla* flower earlier than plants of 'Rio White'.
3. Plants of the new *Mandevilla* and 'Rio White' differ in flower color as plants of 'Rio White' have white-colored flowers.

Plants of the new *Mandevilla* can be compared to plants of the male parent. 'Rio Deep Red'. Plants of the new *Mandevilla* differ primarily from plants of 'Rio Deep Red' in the following characteristics:

1. Plants of the new *Mandevilla* are larger than plants of 'Rio Deep Red'.
2. Plants of the new *Mandevilla* have larger leaves than plants of 'Rio Deep Red'.
3. Plants of the new *Mandevilla* have larger and more open flowers than plants of 'Rio Deep Red'.
4. Plants of the new *Mandevilla* and 'Rio Deep Red' differ in flower color as flowers of plants of 'Rio Deep Red' have red-colored flowers.

Plants of the new *Mandevilla* can also be compared to plants of *Mandevilla hybrida* 'Sunparapibra', disclosed in U.S. Plant Pat. No. 19,649. In side-by-side comparisons plants of the new *Mandevilla* differ primarily from plants 'Sunparapibra' in the following characteristics:

1. Flowers of plants of the new *Mandevilla* are larger and more open than flowers of plants of 'Sunparapibra'.
2. Plants of the new *Mandevilla* and 'Sunparapibra' differ in flower color as flowers of plants of 'Sunparapibra' are more reddish pink in color with darker yellow-colored throats.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Inmanpinli' grown in a container.

The photograph on the second sheet is a close-up view of a typical flowering plant of 'Inmanpinli'.

DETAILED BOTANICAL DESCRIPTION

The aforementioned photographs and following observations, measurements and values describe plants grown during the summer with two plants in 23-cm containers with wooden support frames in a glass-covered greenhouse in Heidesheim, Germany and under cultural practices typical of *Mandevilla* commercial production. During the production of the plants, day temperatures ranged from 20° C. to 47° C. and night temperatures ranged from 8° C. to 25° C. Plants were nine months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'Inmanpinli'.

Parentage:

*Female, or seed, parent.*—*Mandevilla sanderi* 'Rio White', not patented.

*Male, or pollen, parent.*—*Mandevilla sanderi* 'Rio Deep Red', not patented.

Propagation:

*Type*.—By vegetative cuttings.

*Time to initiate roots, summer*.—About three weeks at temperatures ranging from 20° C. to 35° C.

*Time to initiate roots, winter*.—About three weeks at temperatures ranging from 20° C. to 25° C.

*Time to produce a rooted young plant, summer*.—About 20 to 25 days at temperatures ranging from 20° C. to 35° C.

*Time to produce a rooted young plant, winter*.—About 25 to 30 days at temperatures ranging from 20° C. to 25° C.

*Root description*.—Thick, fleshy; typically white in color, actual color of the roots is dependent on substrate composition, water quality, fertilizers, substrate temperature and physiological age of roots.

*Rooting habit*.—Low branching; medium density.

Plant description:

*Plant and growth habit*.—Upright and vining plant habit; vigorous growth habit and rapid growth rate.

*Plant height*.—About 87 cm.

*Plant diameter (spread)*.—About 73.3 cm.

*Lateral branch description*.—Branching habit: Freely branching habit with about two primary lateral branches each with about five secondary lateral branches. Length: About 89.6 cm. Diameter: About 3.5 mm. Internode length: About 6 cm. Aspect: Primary lateral branches, about 40° from vertical; secondary lateral branches, about 25° from primary branch axis. Strength: Strong. Texture and luster: Smooth, glabrous; glossy; becoming woody with development. Color, developing: Close to 144A. Color, developed: Close to 144A; when woody, close to 199A and N199C.

Leaf description:

*Arrangement*.—Opposite, simple.

*Length*.—About 8.2 cm.

*Width*.—About 5 cm.

*Shape*.—Ovate to oblong.

*Apex*.—Short apiculate.

*Base*.—Obtuse to truncate.

*Margin*.—Entire; coarsely undulate.

*Texture and luster, upper surface*.—Smooth, glabrous; glossy.

*Texture and luster, lower surface*.—Smooth, glabrous; slightly glossy to moderately glossy.

*Venation pattern*.—Pinnate.

*Color*.—Developing leaves, upper surface: Darker than between 143A and 144A. Developing leaves, lower surface: Close to 148A. Full expanded leaves, upper surface: Darker than between NN137A and 147A; venation, close to 143B. Fully expanded leaves, lower surface: Close to 146B; venation, close to 144C.

*Petioles*.—Length: About 1.1 cm. Diameter: About 2 mm. Strength: Moderately strong. Texture and luster, upper and lower surfaces: Smooth, glabrous; moderately glossy. Color, upper surface: Close to 143C. Color, lower surface: Close to 144C.

Flower description:

*Flower type and flowering habit*.—Single salverform flowers arranged in axillary cymes; flowers face mostly outwardly; freely flowering habit with about three flowers per inflorescence and about 110 flower buds and open flowers per plant.

*Natural flowering season*.—Plants flower continuously from spring into the autumn in Germany; plants begin flowering about 16 weeks after propagation.

*Flower longevity on the plant*.—About ten days; flowers not persistent.

*Fragrance*.—Faintly fragrant; sweet and pleasant.

*Inflorescence height*.—About 9.5 cm.

*Inflorescence diameter*.—About 9.1 cm.

*Flower buds*.—Length: About 7.1 cm. Diameter: About 1.4 cm. Shape: Narrowly oblanceolate. Texture and luster: Smooth, glabrous; slightly glossy. Color: Close to 62A; towards the base, close to 145C and at the base, close to 145A.

*Flowers*.—Appearance: Flared trumpet, corolla fused and five-parted. Diameter: About 7.8 cm. Depth (length): About 7.9 cm. Throat diameter: About 1.8 cm. Tube length: About 5.2 cm. Tube diameter: Proximally, about 5 mm; distally, about 2 cm.

*Corolla*.—Quantity and arrangement: Five petals arranged in a single whorl; lower 60% portion of the petals are fused into a tube. Petal length: About 9.5 cm. Petal width: About 3.9 cm. Petal shape and appearance: Roughly spatulate. Petal apex: Apiculate. Petal margin: Entire; undulate. Petal texture and luster, upper surface: Smooth, glabrous; velvety; matte. Petal texture and luster, lower surface: Smooth, glabrous; velvety; slightly glossy. Throat and tube texture: Smooth, glabrous. Color: Petal, when opening, upper surface: Close to N57C. Petal, when opening, lower surface: Close to N57D. Petal, fully opened, upper surface: Close to N57C and N57D; towards the throat, close to 69B; "ring" at throat, close to N57B to N57C; venation, similar to lamina; color does not fade with development. Petal, fully opened, lower surface: Slightly lighter than N57D; venation, similar to lamina; color does not fade with development. Throat: Distally, close to 14B; proximally, close to N144D; venation, similar to lamina. Tube: Close to 145A; venation, similar to lamina.

*Calyx*.—Quantity and arrangement: Five sepals arranged in a single whorl. Calyx length: About 8 mm. Calyx diameter: About 6 mm. Sepal length: About 8 mm. Sepal width: About 2 mm. Sepal shape: Narrowly deltoid. Sepal apex: Narrowly acute. Sepal base: Broadly cuneate. Sepal margin: Entire. Sepal texture and luster, upper and lower surfaces: Smooth, glabrous; matte. Sepal color: Immature, upper and lower surfaces: Close to 150D; at the margins and apex, close to 180A. Mature, upper and lower surfaces: Close to 150C; at the apex, close to 180A.

*Peduncles*.—Length: About 4.6 cm. Diameter: About 1.5 mm. Strength: Strong. Aspect: About 20° from lateral branch axis. Texture and luster: Smooth, glabrous; glossy. Color: Close to 144A.

*Pedicels*.—Length: About 1.3 cm. Diameter: About 1.75 mm. Strength: Strong. Aspect: About 15° from peduncle axis. Texture and luster: Smooth, glabrous; moderately glossy. Color: Close to 145B.

*Reproductive organs*.—Stamens: Quantity and arrangement: Typically five; basifixed; anthers connivent. Filament length: About 1 mm. Filament color: Close to 153D. Anther shape: Narrowly oblong. Anther size: About 5 mm by 1.25 mm. Anther color: Close to between 153D and 160A. Pollen amount: None observed. Pistils: Quantity: Typically one. Pistil length: About 2.4 cm. Style length: About 2.2 cm. Style color: Close to 145C. Stigma diameter: About 1.5 mm. Stigma shape: Club-shaped, pointed. Stigma color: Close to 146D; apex, close to 185A. Ovary color: Close to 144C.

*Seeds and fruits*.—Seed and fruit production have not been observed on plants of the new *Mandevilla* to date.

Disease & pest resistance: Plants of the new *Mandevilla* have not been noted to be resistant to pathogens and pests common to *Mandevilla* plants to date.

Temperature tolerance: Plants of the new *Mandevilla* have been observed to tolerate temperatures ranging from about 5° C. to about 48° C. and to be suitable for USDA Hardiness Zones 9 to 13.

It is claimed:

1. A new and distinct *Mandevilla* plant named 'Inmanpinli' as illustrated and described.

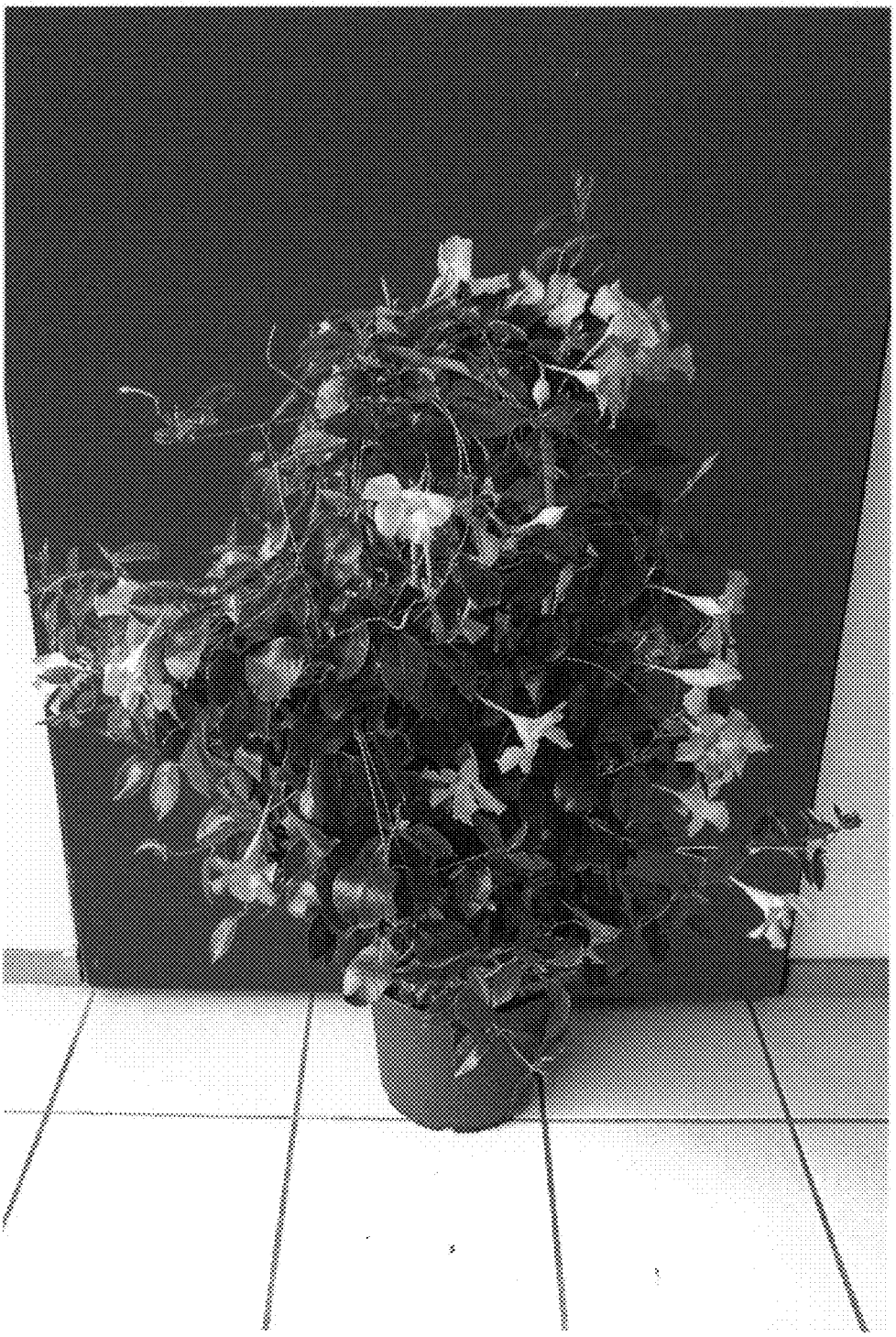

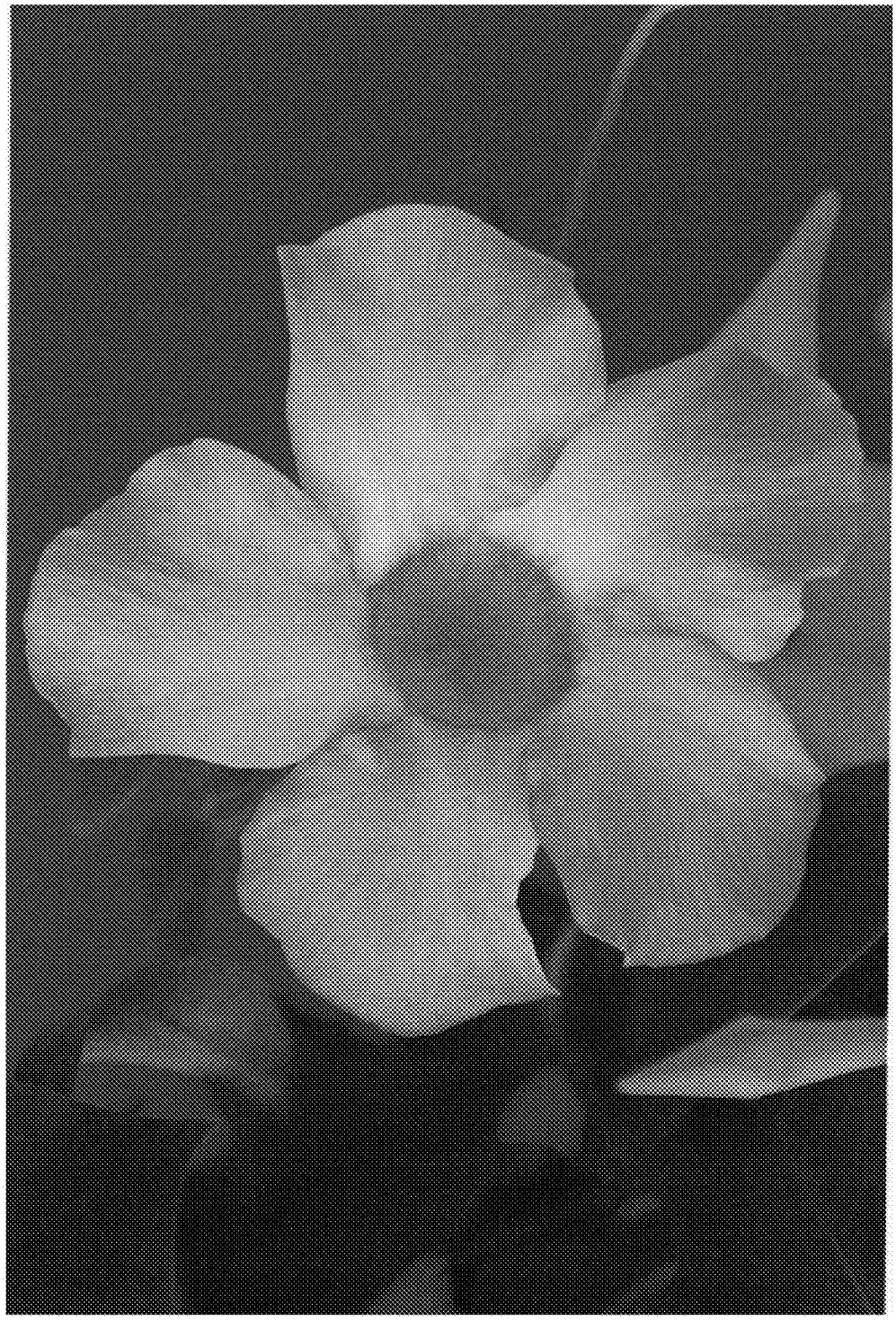

* * * * *